United States Patent [19]

Lunkenheimer et al.

[11] 4,248,886
[45] Feb. 3, 1981

[54] COMBATING FUNGI WITH N-OXALYL-N-PHENYL-AMINOACIDS AND ESTERS THEREOF

[75] Inventors: Winfried Lunkenheimer, Wuppertal; Wilhelm Brandes, Leichlingen, both of Fed. Rep. of Germany

[73] Assignee: Bayer Aktiengesellschaft, Leverkusen, Fed. Rep. of Germany

[21] Appl. No.: 62,400

[22] Filed: Jul. 31, 1979

[30] Foreign Application Priority Data

Aug. 18, 1978 [DE] Fed. Rep. of Germany ....... 2836158

[51] Int. Cl.³ .................... A01N 37/46; A01N 43/20; C07C 101/44; C07D 303/40
[52] U.S. Cl. .............................. 424/278; 260/348.43; 260/348.45; 260/348.46; 260/455 R; 260/465 D; 560/43; 560/44; 424/278; 424/301; 424/304; 424/309
[58] Field of Search .......... 260/465 D, 455 R, 348.46; 560/44; 424/309, 301, 304, 278

[56] References Cited

U.S. PATENT DOCUMENTS

| 3,780,090 | 12/1978 | Akiba et al. ................ 260/471 A |
| 4,025,648 | 5/1977 | Hubele ............................. 424/309 |
| 4,093,738 | 6/1978 | Hubele ............................. 424/309 |
| 4,098,895 | 7/1978 | Hubele et al. ................... 424/309 X |

FOREIGN PATENT DOCUMENTS 2648074 4/1978 Fed. Rep. of Germany.
2819878 11/1978 Fed. Rep. of Germany.

*Primary Examiner*—Dolph H. Torrence
*Attorney, Agent, or Firm*—Sprung, Felfe, Horn, Lynch & Kramer

[57] ABSTRACT

N-oxalyl-N-phenyl-aminoacid or ester thereof of the formula

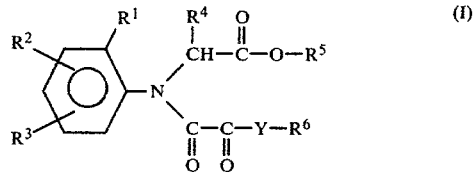

in which:
R¹ represents hydrogen, alkyl or halogen,
R² represents hydrogen or alkyl,
R³ represents hydrogen or alkyl,
R⁴ represents hydrogen, alkyl or optionally substituted phenyl,
R⁵ represents hydrogen, alkyl, cyanoalkyl, alkenyl, alkynyl, halogenoalkyl, cycloalkyl, cycloalkylalkyl, alkoxyalkyl, alkoxyalkoxyalkyl, alkoxycarbonylalkyl, alkylthioalkyl, alkylsulphinylalkyl, alkylsulphonylalkyl, dialkylaminoalkyl, optionally substituted aryl or optionally substituted aralkyl and
R⁶ represents alkyl, cyanoalkyl, alkenyl, alkynyl, halogenoalkyl, cycloalkyl, cycloalkylalkyl, alkoxyalkyl, alkoxyalkoxyalkyl, alkoxycarbonylalkyl, alkylthioalkyl, alkylsulphinylalkyl, alkylsulphonylalkyl, dialkylaminoalkyl, optionally substituted aryl, optionally substituted aralkyl, optionally substituted aroxyalkyl, epoxyalkyl or a grouping of the formula

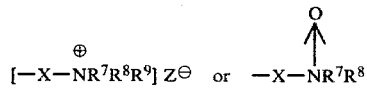

wherein
R⁷, R⁸ and R⁹, which need not be identical, each represent alkyl,
X represents alkylene or alkylidene
Y represents oxygen or sulphur and
Z represents the anion of an inorganic or organic acid,
which possess fungicidal properties.

5 Claims, No Drawings

COMBATING FUNGI WITH N-OXALYL-N-PHENYL-AMINOACIDS AND ESTERS THEREOF

The present invention relates to and has for its objects the provision of particular new N-oxalyl-N-phenyl-aminoacids and esters thereof which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has already been disclosed that zinc ethylene-1,2-bis-dithiocarbamate is a good agent for combating fungal plant diseases (see Phytopathology, 33, 1,113 (1963)). However, its use is only possible with certain limitations, since, if low amounts and low concentrations are used, it does not always exhibit a satisfactory action, in particular when combating species of Phytophthora.

The present invention now provides, as new compounds, the N-oxalyl derivatives of N-phenyl-aminoacids and N-phenyl-aminoacid esters, of the general formula

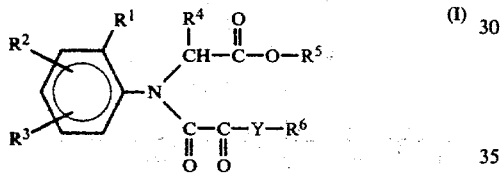

in which
$R^1$ represents hydrogen, alkyl or halogen,
$R^2$ represents hydrogen or alkyl,
$R^3$ represents hydrogen or alkyl,
$R^4$ represents hydrogen, alkyl or optionally substituted phenyl,
$R^5$ represents hydrogen, alkyl, cyanoalkyl, alkenyl, alkynyl, halogenoalkyl, cycloalkyl, cycloalkylalkyl, alkoxyalkyl, alkoxyalkoxyalkyl, alkoxycarbonylalkyl, alkylthioalkyl, alkylsulphinylalkyl, alkylsulphonylalkyl, dialkylaminoalkyl, optionally substituted aryl or optionally substituted aralkyl and
$R^6$ represents alkyl, cyanoalkyl, alkenyl, alkynyl, halogenoalkyl, cycloalkyl, cycloalkylalkyl, alkoxyalkyl, alkoxyalkoxyalkyl, alkoxycarbonylalkyl, alkylthioalkyl, alkylsulphinylalkyl, alkylsulphonylalkyl, dialkylaminoalkyl, optionally substituted aryl, optionally substituted aralkyl, optionally substituted aroxyalkyl, epoxyalkyl or a grouping of the formula

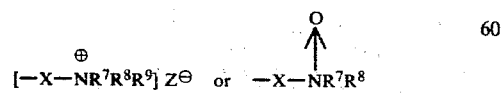

wherein
$R^7$, $R^8$ and $R^9$, which need not be identical, each represent alkyl,
X represents alkylene or alkylidene,
Y represents oxygen or sulphur and
Z represents the anion of an inorganic or organic acid.

They exhibit powerful fungicidal properties.

Preferably, in formula (I), $R^1$ represents hydrogen, straight-chain or branched alkyl with 1 to 4 carbon atoms, fluorine, chlorine or bromine,
$R^2$ represents hydrogen or straight-chain or branched alkyl with 1 to 4 carbon atoms,
$R^3$ represents hydrogen or straight-chain or branched alkyl with 1 to 4 carbon atoms,
$R^4$ represents hydrogen, straight-chain or branched alkyl with 1 to 4 carbon atoms or optionally substituted phenyl [preferred substituents being halogen (especially fluorine, chlorine or bromine), alkyl with 1 to 2 carbon atoms and halogenoalkyl with up to 2 carbon atoms and up to 3 identical or different halogen atoms (preferred halogens being fluorine and chlorine)],
$R^5$ represents hydrogen, straight-chain or branched alkyl or cyanoalkyl, each with 1 to 6 carbon atoms, alkenyl or alkynyl, each with 2 to 4 carbon atoms, halogenoalkyl with 1 to 4 carbon atoms and up to 5 halogen atoms (especially with up to 2 carbon atoms and up to 3 identical or different halogen atoms, preferred halogens being fluorine and chlorine), cycloalkyl with 3 to 7 carbon atoms, cycloalkylalkyl with 3 to 7 carbon atoms in the cycloalkyl part and 1 to 4 carbon atoms in the alkyl part, alkoxyalkyl, alkoxyalkoxyalkyl, alkoxycarbonylalkyl, alkylthioalkyl, alkylsulphinylalkyl and alkylsulphonylalkyl, each with 1 to 4 carbon atoms in each alkyl part, aryl with 6 to 10 carbon atoms (for example phenyl) which is optionally substituted or aralkyl which is optionally substituted in the aryl part and has 6 to 10 carbon atoms in the aryl part and 1 to 4 carbon atoms in the alkyl part (for example benzyl) [preferred substituents on said aryl or aralkyl being halogen (especially fluorine, chlorine or bromine), alkyl with 1 to 2 carbon atoms and halogenoalkyl with up to 2 carbon atoms and up to 3 identical or different halogen atoms (preferred halogens being fluorine and chlorine)], or dialkylaminoalkyl with 1 to 4 carbon atoms in each alkyl part,
$R^6$ represents straight-chain or branched alkyl or cyanoalkyl, each with 1 to 6 carbon atoms, alkenyl or alkynyl, each with 2 to 4 carbon atoms, halogenoalkyl with 1 to 4 carbon atoms and up to 5 halogen atoms (especially with up to 2 carbon atoms and up to 3 identical or different halogen atoms, preferred halogens being fluorine and chlorine), cycloalkyl with 3 to 7 carbon atoms, cycloalkyl-alkyl with 3 to 7 carbon atoms in the cycloalkyl part and 1 to 4 carbon atoms in the alkyl part, alkoxyalkyl, alkoxyalkoxyalkyl, alkoxycarbonylalkyl, alkylthioalkyl, alkylsulphinylalkyl and alkylsulphonylalkyl, each with 1 to 4 carbon atoms in each alkyl part, aryl with 6 to 10 carbon atoms (for example phenyl) which is optionally substituted or aralkyl which is optionally substituted in the aryl part and has 6 to 10 carbon atoms in the aryl part and 1 to 4 carbon atoms in the alkyl part (for example benzyl) [preferred substituents on said aryl or aralkyl being halogen (especially fluorine, chlorine or bromine), alkyl with 1 to 2 carbon atoms and halogenoalkyl with up to 2 carbon atoms and up to 3 identical or different halogen atoms (preferred halogens being fluorine and chlorine)], dialkylaminoalkyl with 1 to 4 carbon atoms in each alkyl part, aroxyalkyl which is optionally substituted in the aryl part and has 6 to 10 carbon atoms in the aryl part and 1 to 4 carbon atoms in the alkyl part [preferred substituents being halogen (especially fluorine, chlorine or bromine), alkyl with 1 to 2 carbon atoms and halogenoalkyl with up to 2 carbon atoms and up to 3 identical or different halogen atoms (preferred halogens being fluorine and chlorine)], epoxyalkyl with a total of 3 to 8 carbon atoms, or a group of the formula

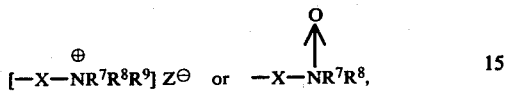

$R^7$, $R^8$ and $R^9$, which need not be identical, each represent alkyl with 1 to 4 carbon atoms, X represents alkylene with 1 to 4 carbon atoms or alkylidene with 2 to 4 carbon atoms, Y represents oxygen or sulphur and Z represents the anion of an inorganic or organic acid.

Surprisingly, the N-oxalyl derivatives of N-phenylaminoacids and N-phenyl-amino acid esters, according to the invention, exhibit a substantially higher fungicidal activity, especially in respect of species of Phytophthora, than zinc ethylene-1,2-bis-dithiocarbamate, known from the prior art, which is a compound of the same type of action. The compounds according to the invention thus represent an enrichment of the art.

Particularly preferred compounds of the formula (I) are those
in which
$R^1$ represents hydrogen, methyl, ethyl, n-propyl, isopropyl, n-butyl, isobutyl, sec.-butyl, tert.-butyl, fluorine, chlorine or bromine, $R^2$ represents hydrogen, methyl, ethyl, n-propyl, isopropyl, n-butyl, isobutyl, sec.-butyl, or tert.-butyl, $R^3$ represents hydrogen, methyl, ethyl, n-propyl, isopropyl, n-butyl, isobutyl, sec.-butyl, or tert.-butyl, $R^4$ represents hydrogen, methyl, or phenyl which is optionally substituted by chlorine and/or by methyl and/or by ethyl, $R^5$ represents hydrogen, methyl, ethyl, n-propyl, isopropyl, n-butyl, isobutyl, sec.-butyl, tert.-butyl, cyanoethyl, vinyl, allyl, propargyl, chloroethyl, cyclopropyl, cyclopropylmethyl, cyclohexyl, cyclohexylmethyl, methoxyethyl, ethoxyethyl, methylthioethyl, ethylthioethyl, methoxyethoxyethyl, butoxycarbonylmethyl, methylsulphinylethyl, ethylsulphinylethyl, methylsulphonylethyl, ethylsulphonylethyl, phenyl or benzyl [either of which is optionally substituted by chlorine and/or methyl and/or ethyl], dimethylaminoethyl or diethylaminoethyl, $R^6$ represents methyl, ethyl, n-propyl, isopropyl, n-butyl, isobutyl, sec.-butyl, tert.-butyl, cyanoethyl, vinyl, allyl, propargyl, chloroethyl, cyclopropyl, cyclopropylmethyl, cyclohexyl, cyclohexylmethyl, methoxyethyl, ethoxyethyl, methylthioethyl, ethylthioethyl, methoxyethoxyethyl, butoxycarbonylmethyl, methylsulphinylethyl, ethylsulphinylethyl, methylsulphonylethyl, ethylsulphonylethyl, phenyl or benzyl [either of which is optionally substituted by chlorine and/or methyl and/or ethyl], dimethylaminoethyl, diethylaminoethyl, phenoxyethyl [in which the phenyl part can optionally be substituted by methyl and/or ethyl], ethylene oxide-methyl, ethylene oxide-ethyl or a group of the formula

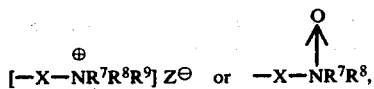

$R^7$, $R^8$ and $R^9$ which need not be identical, each represent methyl or ethyl, X represents methylene, ethylene, ethylidene or propylidene, Y represents oxygen or sulphur and Z represents a halide anion (such as chloride, bromide or iodide) or a nitrate, sulphate, phosphate, acetate, propionate, glycollate, lactate, malonate, tartrate, benzoate, methanesulphonate, p-toluenesulphonate, benzenesulphonate or methylsulphate anion.

Specifically, the following compounds of the general formula (I) may be mentioned in addition to the compounds mentioned later in the preparative examples:

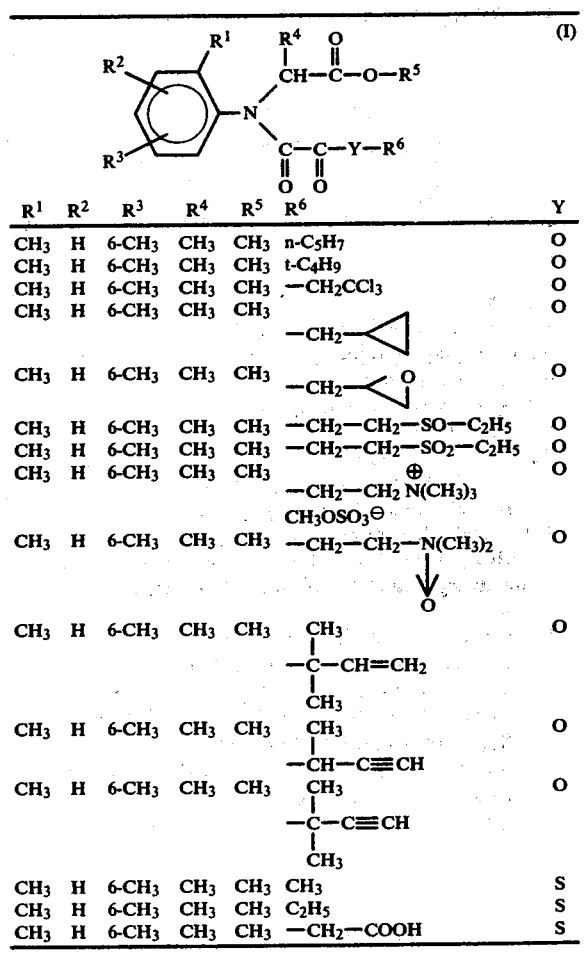

The invention also provides a process for the preparation of an N-oxalyl derivative of an N-phenylaminoacid or N-phenyl-aminoacid ester, of the formula (I), in which an N-phenyl-aminoacid or N-phenyl-aminoacid ester of the general formula

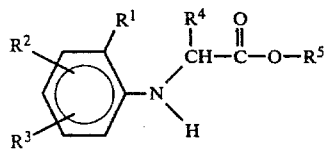 (II), in which
R¹ to R⁵ have the above-mentioned meanings,
(a) is reacted with a chloroglyoxylic acid of the general formula

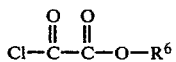 (III), in which
R⁶ has the above-mentioned meaning, in the presence of a solvent and, if appropriate, in the presence of an acid-binding agent and/or in the presence of a catalyst, or
(b) is first reacted with oxalyl chloride, of the formula

 (IV), in the presence of a solvent and, if appropriate, in the presence of an acid-binding agent and/or in the presence of a catalyst, after which the compound thus produced, of the general formula

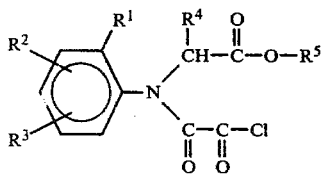 (V), in which
R¹ to R⁵ have the above-mentioned meanings, is reacted with an alcohol or mercaptan of the general formula

H—Y—R⁶     (VI), in which
R⁶ and Y have the above-mentioned meanings, in the presence of a solvent and, if appropriate, in the presence of an acid-binding agent and/or in the presence of a catalyst.

If, for example, N-(2,6-xylyl)-alanine methyl ester and methoxalyl chloride are used as starting materials in process variant (a), the course of the reaction can be represented by the following equation:

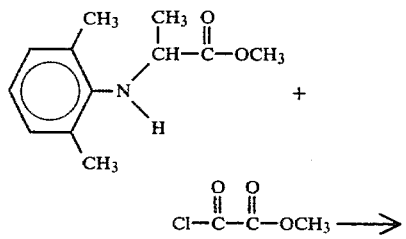

If N-(2,6-xylyl)-alanine methyl ester, oxalyl chloride and methylglycol are used as starting materials in process variant (b), the course of the reaction can be represented by the following equation:

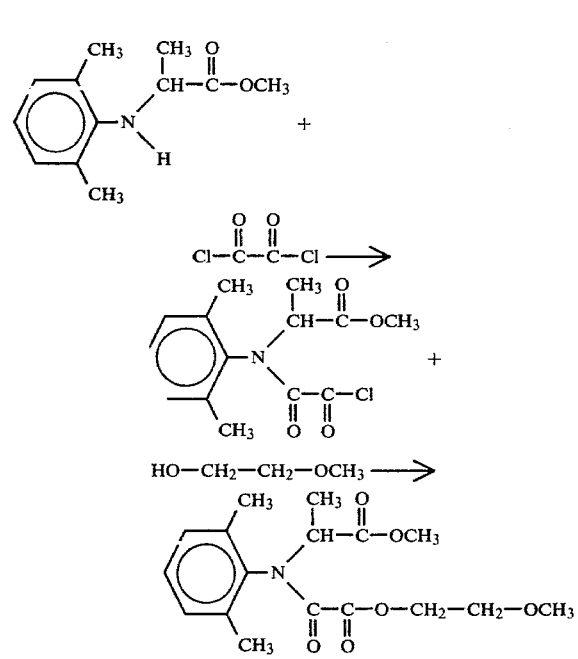

The formula (II) provides a general definition of the N-phenyl-aminoacids and N-phenyl-aminoacid esters to be used as starting materials. In this formula, R¹ to R⁵ preferably have the meanings which have already been mentioned as preferences in connection with the compounds of the formula (I).

The N-phenyl-aminoacids and N-phenyl-aminoacid esters of the formula (II) are in general known (see, inter alia, German Offenlegungsschrift (German Published Specification) No. 2,648,074 and U.S. Pat. No. 3,780,090). Compounds which have not yet been disclosed in the literature can be obtained by the processes described in the said publications, for example by reacting corresponding anilines with corresponding α-halogenocarboxylic acids or α-halogenocarboxylic acid esters, for example chloroacetic acid or chloroacetic acid esters, or α-chloropropionic acid or α-chloropropionic acid esters, in the presence of an acid-binding agent, for example potassium carbonate, and in the presence of an inert organic solvent, for example dimethylformamide, and, if appropriate, in the presence of a catalyst, for example potassium iodide, at temperatures between 20° and 160° C. The N-phenyl-aminoacid esters of the formula (II) can also be obtained by esterifying N-phenyl-aminoacids with the corresponding alcohols in accordance with known methods, for example in the presence of boron trifluoride.

The following may be mentioned as examples of the starting materials of the formula (II): N-(2,6-dimethylphenyl)-alanine(glycine), N-(2,6-dimethylphenyl)-alanine(glycine) methyl ester, N-(2,6-dimethylphenyl)-alanine(glycine) ethyl ester, N-(2,6-dimethylphenyl)-alanine(glycine) isopropyl ester, N-(2,6-dimethylphenyl)-alanine(glycine) 2-methoxyethyl ester, N-(2,6-dimethylphenyl)-alanine(glycine) 2-ethoxyethyl ester, N-(2,6-dimethylphenyl)-alanine(glycine) cyclohexyl ester, N-(2,6-dimethylphenyl)-alanine(glycine) cyclohexylmethyl ester, N-(2,6-dimethylphenyl)-alanine(glycine) cyclopropylmethyl ester, N-(2,6-dimethylphenyl)-alanine(glycine) 2-methylthioethyl ester, N-(2,6-dimethylphenyl)-alanine(glycine) 2-methylsulphinylethyl ester, N-(2,6-dimethylphenyl)-alanine(glycine) 2-methylsulphonylethyl ester, N-(2,6-dimethylphenyl)-alanine(glycine) 2-dimethylaminoethyl ester, N-(2,6-dimethylphenyl)-alanine(glycine) benzyl ester, N-(2,6-dimethylphenyl)-alanine(glycine) 2,4-dichlorobenzyl ester, N-(2,6-dimethylphenyl)-alanine(glycine) 2-(2-methoxyethoxy)-ethyl ester, N-(2,6-dimethylphenyl)-alanine(glycine) 2-cyanomethyl ester, N-(2,6-dimethylphenyl)-alanine(glycine) phenyl ester, N-(2,6-dimethylphenyl)-alanine(glycine) allyl ester, N-(2,6-dimethylphenyl)-alanine(glycine) propargyl ester, N-(2,6-dimethylphenyl)-alanine(glycine) chloroethyl ester, N-(2,6-dimethylphenyl)-alanine(glycine) 2,2,2-trichloroethyl ester, N-(2,6-dimethylphenyl)-alanine(glycine) 2-ethylthioethyl ester, N-(2,6-dimethylphenyl)-alanine(glycine) 2-ethylsulphinylethyl ester, N-(2,6-dimethylphenyl)-alanine(glycine) 2-ethylsulphonylethyl ester, N-(2,6-dimethylphenyl)-alanine(glycine) butoxycarbonylmethyl ester, N-(2,6-dimethylphenyl)-alanine(glycine) 1-ethoxycarbonylethyl ester, N-(2-ethyl-6-methylphenyl)-alanine(glycine), N-(2-ethyl-6-methylphenyl)-alanine(glycine) methyl ester, N-(2-ethyl-6-methylphenyl)-alanine(glycine) ethyl ester, N-(2-ethyl-6-methylphenyl)-alanine(glycine) isopropyl ester, N-(2-ethyl-6-methylphenyl)-alanine(glycine) 2-methoxyethyl ester, N-(2-ethyl-6-methylphenyl)-alanine(glycine) 2-ethoxyethyl ester, N-(2-ethyl-6-methylphenyl)-alanine(glycine) cyclohexyl ester, N-(2-ethyl-6-methylphenyl)-alanine(glycine) cyclohexylmethyl ester, N-(2-ethyl-6-methylphenyl)-alanine(glycine) cyclopropylmethyl ester, N-(2-ethyl-6-methylphenyl)-alanine(glycine) 2-methylthioethyl ester, N-(2-ethyl-6-methylphenyl)-alanine(glycine) 2-methylsulphinylethyl ester, N-(2-ethyl-6-methylphenyl)-alanine(glycine) 2-methylsulphonylethyl ester, N-(2-ethyl-6-methylphenyl)-alanine(glycine) 2-dimethylaminoethyl ester, N-(2-ethyl-6-methylphenyl)-alanine(glycine) benzyl ester, N-(2-ethyl-6-methylphenyl)-alanine(glycine) 2,4-dichlorobenzyl ester, N-(2-ethyl-6-methylphenyl)-alanine(glycine) 2-(2-methoxyethoxy)-ethyl ester, N-(2-ethyl-6-methylphenyl)-alanine(glycine) 2-cyanoethyl ester, N-(2-ethyl-6-methylphenyl)-alanine(glycine) phenyl ester, N-(2-ethyl-6-methylphenyl)-alanine(glycine) allyl ester, N-(2-ethyl-6-methylphenyl)-alanine(glycine) propargyl ester, N-(2-ethyl-6-methylphenyl)-alanine(glycine) 2-chloroethyl ester, N-(2-ethyl-6-methylphenyl)-alanine(glycine) 2,2,2-trichloroethyl ester, N-(2-ethyl-6-methylphenyl)-alanine(glycine) 2-ethylthioethyl ester, N-(2-ethyl-6-methylphenyl)-alanine(glycine) 2-ethylsulphinylethyl ester, N-(2-ethyl-6-methylphenyl)-alanine(glycine) 2-ethylsulphonylethyl ester, N-(2-ethyl-6-methylphenyl)-alanine(glycine) 2-butoxycarbonylmethyl ester, N-(2-ethyl-6-methylphenyl)-alanine(glycine) 1-ethoxycarbonylethyl ester, N-(2-chloro-6-methylphenyl)-alanine(glycine), N-(2-chloro-6-methylphenyl)-alanine(glycine) methyl ester, N-(2-chloro-6-methylphenyl)-alanine(glycine) ethyl ester, N-(2-chloro-6-methylphenyl)-alanine(glycine) 2-methoxyethyl ester, N-(2-chloro-6-methylphenyl)-alanine(glycine) 2-ethoxyethyl ester, N-(2-chloro-6-methylphenyl)-alanine(glycine) 2-methylthioethyl ester, N-(2-chloro-6-methylphenyl)-alanine(glycine) 2-dimethylaminoethyl ester, N-(2-chloro-6-methylphenyl)-alanine(glycine) 2-cyanoethyl ester, N-(2-chloro-6-methylphenyl)-alanine(glycine) allyl ester, N-(2-chloro-6-methylphenyl)-alanine(glycine) propargyl ester, N-(2-chloro-6-methylphenyl)-alanine(glycine) 2,2,2-trichloroethyl ester, N-(2-chloro-6-methylphenyl)-alanine(glycine) 1-ethoxycarbonylethyl ester, N-(2-chloro-6-ethylphenyl)-alanine(glycine), N-(2-chloro-6-ethylphenyl)-alanine(glycine) methyl ester, N-(2-chloro-6-ethylphenyl)-alanine(glycine) ethyl ester, N-(2-chloro-6-ethylphenyl)-alanine(glycine) 2-methoxyethyl ester, N-(2-chloro-6-ethylphenyl)-alanine(glycine) 2-methylthioethyl ester, N-(2-chloro-6-ethylphenyl)-alanine(glycine) 2-dimethylaminoethyl ester, N-(2-chloro-6-ethylphenyl)-alanine(glycine) 2-cyanoethyl ester, N-(2-chloro-6-ethylphenyl)-alanine(glycine) allyl ester, N-(2-chloro-6-ethylphenyl)-alanine(glycine) propargyl ester, N-(2-chloro-6-ethylphenyl)-alanine(glycine) 2,2,2-trichloroethyl ester, N-(2-chloro-6-ethylphenyl)-alanine(glycine) 1-ethoxycarbonylethyl ester, N-(2,4,6-trimethylphenyl)-alanine(glycine), N-(2,4,6-trimethylphenyl)-alanine(glycine) methyl ester, N-(2,4,6-trimethylphenyl)-alanine(glycine) ethyl ester, N-(2,4,6-trimethylphenyl)-alanine(glycine) 2-methoxyethyl ester, N-(2,4,6-trimethylphenyl)-alanine(glycine) 2-methylthioethyl ester, N-(2,4,6-trimethylphenyl)-alanine(glycine) 2-dimethylaminoethyl ester, N-(2,4,6-trimethylphenyl)-alanine(glycine) 2-cyanoethyl ester, N-(2,4,6-trimethylphenyl)-alanine(glycine) allyl ester, N-(2,4,6-trimethylphenyl)-alanine(glycine) propargyl ester, N-(2,4,6-trimethylphenyl)alanine(glycine) 2,2,2-trichloroethyl ester, N-(2,4,6-trimethylphenyl)-alanine(glycine) 1-ethoxycarbonylethyl ester, N-(2-ethyl-4,6-dimethylphenyl)-alanine(glycine), N-(2-ethyl-4,6-dimethylphenyl)-alanine(glycine) methyl ester, N-(2-ethyl-4,6-dimethylphenyl)-alanine(glycine) ethyl ester, N-(2-ethyl-4,6-dimethylphenyl)-alanine(glycine) methoxyethyl ester, N-(2-ethyl-4,6-dimethylphenyl)-alanine(glycine) methylthioethyl ester, N-(2-ethyl-4,6-dimethylphenyl)-alanine(glycine) dimethylaminoethyl ester, N-(2-ethyl-4,6-dimethylphenyl)-alanine(glycine) 2-cyanoethyl ester, N-(2-ethyl-4,6-dimethylphenyl)-alanine(glycine) allyl ester, N-(2-ethyl-4,6-dimethylphenyl)-alanine(glycine) propargyl ester, N-(2-ethyl-4,6-dimethylphenyl)-alanine(glycine) 2,2,2-trichloroethyl ester, N-(2-ethyl-4,6-dimethylphenyl)-alanine(glycine 1-ethoxycarbonylethyl ester, N-(2,6-diethyl-4-methylphenyl)-alanine(glycine), N-(2,6-diethyl-4-methylphenyl)-alanine(glycine) methyl ester, N-(2,6-diethyl-4-methylphenyl)-alanine(glycine) 2-methoxyethyl ester, N-(2,6-diethyl-4-methylphenyl)-alanine(glycine) 2-methylthioethyl ester, N-(2,6-diethyl-4-methylphenyl)-alanine(glycine) 2-dimethylaminoethyl ester, N-(2,6-diethyl-4-methylphenyl)-alanine(glycine) 2-cyanoethyl ester, N-(2,6-diethyl-4-methylphenyl)-alanine(glycine) allyl ester, N-(2,6-diethyl-4-methylphenyl)-alanine(glycine) propargyl ester, N-(2,6-diethyl-4-methylphenyl)-alanine(glycine) 2,2,2-trichloroethyl ester, N-(2,6-diethyl-4-methylphenyl)-alanine(glycine) 1-ethoxycarbonylethyl ester, N-(2,6-diisopropylphenyl)-alanine(glycine), N-(2,6-diisopropylphenyl)-alanine(glycine) methyl ester, N-(2,6-diisopropylphenyl)-alanine(glycine) ethyl ester, N-(2,6-diisopropylphenyl)-alanine(glycine) methoxyethyl ester, N-(2,6-diisopropylphenyl)-alanine(glycine) methylthioethyl ester, N-(2,6-diisopropylphenyl)-alanine(glycine) 2-dimethylaminoethyl ester, N-(2,6-diisopropylphenyl)-alanine(glycine) 2-cyanoethyl ester, N-(2,6-diisopropylphenyl)-alanine(glycine) allyl ester, N-(2,6-diisopropylphenyl)-alanine(glycine) propargyl ester, N-(2,6-diisopropylphenyl)-alanine(glycine) 2,2,2-trichloroethyl ester, N-(2,6-diisopropylphenyl)-alanine(glycine) 1-ethoxycarbonylethyl ester, N-(2-methylphenyl)-alanine(glycine), N-(2-methylphenyl)-alanine(glycine) methyl ester, N-(2-methylphenyl)-alanine(glycine) ethyl ester, N-(2-methylphenyl)-alanine(glycine) 2-methoxyethyl ester, N-(2-methylphenyl)-alanine(glycine) 2-methylthioethyl ester, N-(2-methylphenyl-alanine(glycine) 2-dimethylaminoethyl ester, N-(2-methylphenyl)-alanine(glycine) 2-cyanoethyl ester, N-(2-methylphenyl)-alanine(glycine) allyl ester, N-(2-methylphenyl)-alanine(glycine) propargyl ester, N-(2-methylphenyl)-alanine(glycine) 2,2,2-trichloroethyl ester, N-(2-methylphenyl)-alanine(glycine) 1-ethoxycarbonylethyl ester, N-(2-ethylphenyl)-alanine(glycine), N-(2-ethylphenyl)-alanine(glycine) methyl ester, N-(2-ethylphenyl)-alanine(glycine) ethyl ester, N-(2-ethylphenyl)-alanine(glycine) 2-methoxyethyl ester, N-(2-ethylphenyl)-alanine(glycine) 2-methylthioethyl ester, N-(2-ethylphenyl)-alanine(glycine) 2-cyanoethyl ester, N-(2-ethylphenyl)-alanine(glycine) allyl ester, N-(2-ethylphenyl)-alanine(glycine) propargyl ester, N-(2-ethylphenyl)-alanine(glycine) 2,2,2-trichloroethyl ester, N-(2-ethylphenyl)-alanine(glycine) 1-ethoxycarbonylethyl ester, N-(2,3-dimethylphenyl)-alanine(glycine), N-(2,3-dimethylphenyl)-alanine(glycine) methyl ester, N-(2,3-dimethylphenyl)-alanine(glycine) ethyl ester, N-(2,3-dimethylphenyl)-alanine(glycine) 2-methoxyethyl ester, N-(2,3-dimethylphenyl)-alanine(glycine) 2-methylthioethyl ester, N-(2,3-dimethylphenyl)-alanine(glycine) 2-dimethylaminoethyl ester, N-(2,3-dimethylphenyl)-alanine(glycine) 2-cyanoethyl ester, N-(2,3-dimethylphenyl)-alanine(glycine) allyl ester, N-(2,3-dimethylphenyl)-alanine(glycine) propargyl ester, N-(2,3-dimethylphenyl)-alanine(glycine) 2,2,2-trichloroethyl ester, N-(2,3-dimethylphenyl)-alanine(glycine) 1-ethoxycarbonylethyl ester, N-(2,5-dimethylphenyl)-alanine(glycine), N-(2,5-dimethylphenyl)-alanine(glycine) methyl ester, N-(2,5-dimethylphenyl)-alanine(glycine) ethyl ester, N-(2,5-dimethylphenyl)-alanine(glycine) 2-methoxyethyl ester, N-(2,5-dimethylphenyl)-alanine(glycine) 2-methylthioethyl ester, N-(2,5-dimethylphenyl)-alanine(glycine) 2-dimethylaminoethyl ester, N-(2,5-dimethylphenyl)-alanine(glycine) 2-cyanoethylester, N-(2,5-dimethylphenyl)-alanine(glycine) allyl ester, N-(2,5-dimethylphenyl)-alanine(glycine propargyl ester, N-(2,5-dimethylphenyl)-alanine(glycine) 2,2,2-trichloroethyl ester, N-(2,5-dimethylphenyl)-alanine(glycine) 1-ethoxycarbonylethyl ester, N-(2,4-dimethylphenyl)-alanine(glycine), N-(2,4-dimethylphenyl)-alanine(glycine) methyl ester, N-(2,4-dimethylphenyl)-alanine(glycine) ethyl ester, N-(2,4-dimethylphenyl)-alanine(glycine) 2-methoxyethyl ester, N-(2,4-dimethylphenyl)-alanine(glycine) 2-methylthioethyl ester, N-(2,4-dimethylphenyl)-alanine(glycine) 2-dimethylaminoethyl ester, N-(2,4-dimethylphenyl)-alanine(glycine) 2-cyanoethyl ester, N-(2,4-dimethylphenyl)-alanine(glycine) allyl ester, N-(2,4-dimethylphenyl)-alanine(glycine) propargyl ester, N-(2,4-dimethylphenyl)-alanine(glycine) 2,2,2-trichloroethyl ester, N-(2,4-dimethylphenyl)-alanine(glycine) 1-ethoxycarbonylethyl ester, N-(2-isopropylphenyl)-alanine(glycine), N-(2-isopropylphenyl)-alanine(glycine) methyl ester, N-(2-isopropylphenyl)-alanine(glycine) ethyl ester, N-(2-isopropylphenyl)-alanine(glycine) 2-methoxyethyl ester, N-(2-isopropylphenyl)-alanine(glycine) 2-methylthioethyl ester, N-(2-isopropylphenyl)-alanine(glycine) 2-dimethylaminothyl ester, N-(2-isopropylphenyl)-alanine(glycine) 2-cyanoethyl ester, N-(2-isopropylphenyl)-alanine(glycine) allyl ester, N-(2-isopropylphenyl)-alanine(glycine) propargyl ester, N-(2-isopropylphenyl)-alanine(glycine) 2,2,2-trichloroethyl ester, N-(2-isopropylphenyl)-alanine(glycine) 1-ethoxycarbonylethyl ester, N-(2,4,5-trimethylphenyl)-alanine(glycine), N-(2,4,5-trimethylphenyl)-alanine(glycine) methyl ester, N-(2,4,5-trimethylphenyl)-alanine(glycine) ethyl ester, N-(2,4,5-trimethylphenyl)-alanine(glycine) 2-methoxyethyl ester, N-(2,4,5-trimethylphenyl)-alanine(glycine) 2-methylthioethyl ester, N-(2,4,5-trimethylphenyl)-alanine(glycine) 2-dimethylaminoethyl ester, N-(2,4,5-trimethylphenyl)-alanine(glycine) 2-cyanoethyl ester, N-(2,4,5trimethylphenyl)-alanine(glycine) allyl ester, N-(2,4,5-trimethylphenyl)-alanine(glycine) propargyl ester, N-(2,4,5-trimethylphenyl)-alanine(glycine) 2,2,2-trichloroethyl ester, N-(2,4,5-trimethylphenyl)-alanine(glycine) 1-ethoxycarbonylethyl ester, N-(2,3,5-trimethylphenyl)-alanine(glycine), N-(2,3,5-trimethylphenyl)-alanine(glycine) methyl ester, N-(2,3,5-trimethylphenyl)-alanine(glycine) ethyl ester, N-(2,3,5-trimethylphenyl)-alanine(glycine) 2-methoxyethyl ester, N-(2,3,5-trimethylphenyl)-alanine(glycine) 2-methylthioethyl ester, N-(2,3,5-trimethylphenyl)-alanine(glycine) 2-dimethylaminoethyl ester, N-(2,3,5-trimethylphenyl)-alanine(glycine) 2-cyanoethyl ester, N-(2,3,5-trimethylphenyl)-alanine(glycine) allyl ester, N-(2,3,5-trimethylphenyl)-alanine(glycine) propargyl ester, N-(2,3,5-trimethylphenyl)-alanine(glycine) 2,2,2-trichloroethyl ester, N-(2,3,5-trimethylphenyl)-alanine(glycine) 1-ethoxycarbonylethyl ester, N-(2,3,6-trimethylphenyl)-alanine(glycine), N-(2,3,6-trimethylphenyl)-alanine(glycine) methyl ester, N-(2,3,6-trimethylphenyl)-alanaine(glycine) ethyl ester, N-(2,3,6-trimethylphenyl)-alanine(glycine) 2-methoxyethyl ester, N-(2,3,6-trimethylphenyl)-alanine(glycine) 2-dimethylaminoethyl ester, N-(2,3,6-trimethylphenyl)-alanine(glycine) 2-cyanoethyl ester, N-(2,3,6-trimethylphenyl)-alanine(glycine) allyl ester, N-(2,3,6-trimethylphenyl)-alanine(glycine) propargyl ester, N-(2,3,6-trimethylphenyl)-alanine(glycine) 2,2,2-trichloroethyl ester, N-(2,3,6-trimethylphenyl)-alanine(glycine) 1-ethoxycarbonylethyl ester, N-(2-sec.-butylphenyl)-alanine(glycine), N-(2-sec.-butylphenyl)-alanine(glycine) methyl ester, N-(2-sec.-butylphenyl)-alanine(glycine) ethyl ester, N-(2-sec.-butylphenyl)-alanine(glycine) 2-methoxyethyl ester, N-(2-sec.-butylphenyl)-alanine(glycine) 2-methylthioethyl ester, N-(2-sec.-butylphenyl)-alanine(glycine) 2-dimethylaminoethyl ester, N-(2-sec.-butylphenyl)-alanine(glycine) 2-cyanoethyl ester, N-(2-sec.-butylphenyl)-alanine(glycine) allyl ester, N-(2-sec.-butylphenyl)-alanine(glycine) propargyl ester, N-(2-sec.-butylphenyl)-alanine(glycine) 2,2,2-trichloroethyl ester and N-(2-sec.-butylphenyl)-alanine(glycine) 1-ethoxycarbonylethyl ester.

The formula (III) provides a general definition of the chloroglyoxylic acid esters additionally to be used as starting materials for process variant (a). In this formula, $R^6$ preferably has the meanings which have already been mentioned as preferences in connection with the compounds of the formula (I).

Chloroglyoxylic acid esters of the formula (III) are known can be prepared by reaction of oxalyl chloride with alcohols in accordance with known processes (see G. v. Frank and W. Caro, Ber.dtsch.chem.Ges. 63, 1,532 (1930); S. J. Rhoads and R. E. Michel, J. Am. chem. Soc. 85, 585 (1963)).

The following may be mentioned as examples: methoxalyl chloride, ethoxalyl chloride, isopropoxalyl chloride, phenoxalyl chloride, methylphenoxalyl chloride, dimethylphenoxalyl chloride, diethylphenoxalyl chloride, methoxyethoxalyl chloride, methoxyethoxyethoxalyl chloride, cyanoethoxalyl chloride, ethylthioethoxalyl chloride, phenoxyethoxalyl chloride, allyloxalyl chloride, propargyloxalyl chloride, chloroethoxalyl chloride, cycloyhexyloxalyl chloride and benzoxalyl chloride.

Oxalyl chloride, additionally to be used as a starting material for process variant (b), is defined by formula (IV). Oxalyl chloride is a generally known compound in organic chemistry.

Formula (VI) provides a general definition of the alcohols and mercaptans additionally to be used as starting materials for process variant (b). In this formula, $R^6$ and Y preferably have the meanings which have already been mentioned as preferences in connection with the compounds of the formula (I).

The alcohols and mercaptans of the formula (VI) are generally known compounds in organic chemistry. The following may be mentioned as examples: methyl alcohol, ethyl alcohol, isopropyl alcohol, methylmercaptan, butylmercaptan, methylglycol, O-methyl-diethylene glycol, 2-cyanoethanol, butyl glycollate, 2-ethylthioethanol, 2-phenoxyethanol, 2-dimethylaminoethanol, propargyl alcohol, allyl alcohol, 2-chloroethanol, 2,2,2-trichloroethanol, cyclohexanol, benzyl alcohol, propyl alcohol, tert.-butyl alcohol, cyclopropylmethyl alcohol, 2-butyn-2-ol, 2-methyl-3-butyn-2-ol, 2-methyl-3-butyn-2-ol, ethylmercaptan and mercaptoacetic acid.

Inert organic solvents are preferred as solvents for the reaction according to the invention, in accordance with process variants (a) and (b). The preferred solvents include ketones, such as diethyl ketone and especially acetone and methyl isobutyl ketone; nitriles, such as propionitrile and especially acetonitrile; ethers, such as tetrahydrofuran or dioxane; aliphatic and aromatic hydrocarbons, such as petroleum ether, benzene, toluene or xylene; halogenated hydrocarbons, such as methylene chloride, carbon tetrachloride, chloroform or chlorobenzene; and esters, such as ethyl acetate.

Process variants (a) and (b) according to the invention can, if appropriate, be carried out in the presence of an acid-binding agent (hydrogen chloride acceptor); any of the customary acid-binding agents can be used for this purpose. These include organic bases, preferably tertiary amines, for example triethylamine, and also inorganic bases, for example alkali metal hydroxides and alkali metal carbonates. A suitable catalyst is, in particular, dimethylformamide.

The reaction temperatures for carrying out process variants (a) and (b) according to the invention can be varied within a substantial range. In general, the reaction is carried out at from 0° to 120° C., preferably from 20° to 100° C.

In carrying out process variant (a) according to the invention, preferably 1 to 1.5 moles of chloroglyoxylic acid ester of the formula (III) and, where an acidbinding agent is used, from 1 to 1.5 moles of the latter, are employed per mole of the compound of the formula (II). The compounds of the formula (I) are isolated in the usual manner.

In carrying out process variant (b) according to the invention, preferably 2 moles of oxalyl chloride of the formula (IV) and about 1.1 moles of alcohol or mercaptan of the formula (VI) are employed per mole of the compound of the formula (II). The compounds of the formula (I) are isolated in the usual manner.

According to a particular embodiment, compounds of the formula (I), in which $R^6$ represents the $[-X-N^{\oplus}R^7R^8R^9]Z^{\ominus}$ grouping, can be obtained by reacting corresponding compounds according to the invention, in which $R^6$ represents a tertiary amine, with alkyl halides in the presence of a polar organic solvent, for example acetonitrile or nitromethane, at temperatures between 20° and 120° C., preferably at the boiling point of the particular solvent, and, if desired, replacing the halide in the resulting salts, in a manner which is in itself known, by another anion, by converting the halides of the formula (I) to the corresponding hydroxides, for example by means of a base or of an anion exchange resin, and then reacting the hydroxides with the corresponding acid.

In another particular embodiment, compounds of the formula (I), in which $R^6$ represents the

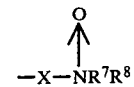

grouping, can be obtained by reacting corresponding compounds according to the invention, in which $R^6$ represents a tertiary amine, in a manner which is in itself known with peroxides, for example, hydrogen peroxide, tert.-butyl hydroperoxide or 3-chloroperbenzoic acid, if appropriate in the presence of a catalyst, for example a vanadium, molybdenium or titanium compound, and, if appropriate, in the presence of an organic solvent, for example glacial acetic acid or methylene chloride, at temperatures between 20° and 80° C., to give the N-oxides.

In a further particular embodiment, compounds of the formula (I), in which $R^6$ represents epoxyalkyl, can be obtained by epoxidizing corresponding compounds according to the invention, in which $R^6$ represents alkenyl, in a manner which is in itself known, by treatment with peracids, for example peracetic acid, perbenzoic acid or trifluoroperacetic acid.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Comycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating downy mildew fungi, for instance the causative organism of blight and brown rot of tomato and potato (*Phytophthora infestans*). It should be particularly emphasized that the active compounds according to the invention not only develop a protective action, but also have a systemic action. Thus, it is possible to protect plants against fungal attack when the active compound is fed to the above-ground parts of the plant via the soil and the root or via the seed.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, immersion, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, from 1 to 0.0001% by weight, preferably from 0.5 to 0.001%.

In the treatment of seed, amounts of active compound of 0.001 to 50 g, preferably 0.01 to 10 g, are generally employed per kilogram of seed.

For the treatment of soil, active compound concentrations of 0.00001 to 0.1% by weight, preferably 0.0001 to 0.02%, are generally employed at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative examples:

EXAMPLE 1

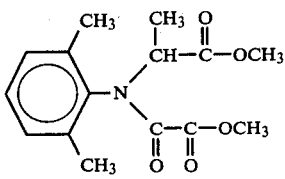 (1)

Process variant (a)

A few drops of dimethylformamide were added to a solution of 20.7 g (0.1 mole) of N-(2,6-xylyl)-alanine methyl ester in 100 ml of toluene, 18.4 g (0.15 mol) of methoxalkyl chloride were added dropwise in 15 minutes at 20°–30° C., and the mixture was stirred for a further 1.5 hours at room temperature. The reaction solution was diluted with ethyl acetate, washed with 20% strength hydrochloric acid, water and 10% strength sodium bicarbonate solution, dried over sodium sulphate and evaporated. The residue was recrystallized from ligroin. This gave 20.8 g (71% of theory) of N-methoxalyl-N-(2,6-xylyl)-alanine methyl estr of melting point 69°–70° C.

EXAMPLE 2

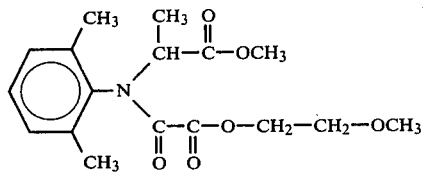 (2)

Process variant (b)

A solution of 10.5 g (0.05 mole) of N-(2,6-xylyl)alanine methyl ester and a few drops of dimethylformamide in 25 ml of toluene was added dropwise in 10 minutes to a solution of 12.7 g (0.01 mole) of oxalyl chloride in 50 ml of toluene at 20°–25° C., and the mixture was stirred for a further 30 minutes at room temperature. It was evaporated and, in order to remove oxalyl chloride, toluene was added and again the mixture was evaporated.

The residue was dissolved in 50 ml of toluene, 4.6 g (0.06 mole) of methylglycol were added dropwise in 7 minutes at 25° C., and the mixture was stirred for 3 hours at 50° C. The reaction solution was diluted with ethyl acetate, washed with 10% strength aqueous pyridine, with 20% strength hydrochloric acid, with water and with 10% strength bicarbonate solution, dried over sodium sulphate and evaporated. The residue was recrystallized from toluene/ligroin (1:15). This gave 10.7 g (64% of theory) of N-(2-methoxyethoxyalkyl)-N-(2,6-xylyl)-alanine methyl ester of melting point 53°–54° C.

The following compounds of the general formula

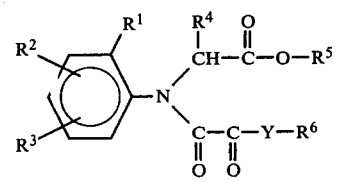 (I)

were obtained analogously:

Table 1

| Compound No. | $R^1$ | $R^2$ | $R^3$ | $R^4$ | $R^5$ | $R^6$ | Y | Melting point (°C.) or Refractive index |
|---|---|---|---|---|---|---|---|---|
| 3 | i-$C_3H_7$ | H | 6-i-$C_3H_7$ | $CH_3$ | —$CH_2$—$CH_2$—$OCH_3$ | $CH_3$ | O | $n_D^{20}$: 1,5011 |
| 4 | $C_2H_5$ | H | 6-$C_2H_5$ | $CH_3$ | —$CH_2$—$CH_2$—$OCH_3$ | $CH_3$ | O | $n_D^{20}$: 1,5038 |
| 5 | $CH_3$ | H | 6-$CH_3$ | $CH_3$ | i-$C_3H_7$ | $CH_3$ | O | $n_D^{20}$: 1,4966 |
| 6 | $CH_3$ | H | 6-$C_2H_5$ | $CH_3$ | —$CH_2$—$CH_2$—$OCH_3$ | $CH_3$ | O | $n_D^{20}$: 1,5028 |
| 7 | $C_2H_5$ | 4-$CH_3$ | 6-$C_2H_5$ | $CH_3$ | —$CH_2$—$CH_2$—$OCH_3$ | $CH_3$ | O | 83–84 |
| 8 | $CH_3$ | 4-$CH_3$ | 6-$CH_3$ | $CH_3$ | —$CH_2$—$CH_2$—$OCH_3$ | $CH_3$ | O | 78–79 |
| 9 | $CH_3$ | 4-$CH_3$ | 6-$C_2H_5$ | $CH_3$ | $C_2H_5$ | $CH_3$ | O | 92–93 |
| 10 | $CH_3$ | 4-$CH_3$ | 6-$C_2H_5$ | $CH_3$ | —$CH_2$—$CH_2$—$OCH_3$ | $CH_3$ | O | 66–67 |
| 11 | $CH_3$ | 4-$CH_3$ | 6-$CH_3$ | $CH_3$ | $CH_3$ | $CH_3$ | O | $n_D^{20}$: 1,5086 |
| 12 | $CH_3$ | 4-$CH_3$ | 6-$C_2H_5$ | $CH_3$ | $CH_3$ | $CH_3$ | O | $n_D^{19}$: 1,5098 |
| 13 | $CH_3$ | H | 5-$CH_3$ | $CH_3$ | $CH_3$ | $CH_3$ | O | $n_D^{20}$: 1,5080 |
| 14 | H | 4-$CH_3$ | H | $CH_3$ | $CH_3$ | $CH_3$ | O | $n_D^{20}$: 1,5086 |
| 15 | $CH_3$ | 3-$CH_3$ | 5-$CH_3$ | $CH_3$ | $CH_3$ | $CH_3$ | O | $n_D^{20}$: 1,5086 |
| 16 | $CH_3$ | H | 6-$CH_3$ | —⟨phenyl⟩ | $CH_3$ | $CH_3$ | O | 115–17 |
| 17 | i-$C_3H_7$ | H | H | $CH_3$ | $CH_3$ | $CH_3$ | O | $n_D^{20}$: 1,5060 |
| 18 | sec.-$C_4H_9$ | H | H | $CH_3$ | $CH_3$ | $CH_3$ | O | $n_D^{20}$: 1,5018 |
| 19 | $CH_3$ | H | H | $CH_3$ | $CH_3$ | $CH_3$ | O | $n_D^{20}$: 1,5071 |
| 20 | $C_2H_5$ | H | H | $CH_3$ | $CH_3$ | $CH_3$ | O | $n_D^{20}$: 1,5071 |
| 21 | $CH_3$ | 3-$CH_3$ | H | $CH_3$ | $CH_3$ | $CH_3$ | O | $n_D^{20}$: 1,5094 |
| 22 | $CH_3$ | H | 6-$CH_3$ | $CH_3$ | $CH_3$ | $C_2H_5$ | O | 89–90 |
| 23 | $CH_3$ | H | 6-$CH_3$ | $CH_3$ | $CH_3$ | $CH_3$ — (2-methylphenyl) | O | $n_D^{19}$: 1,5323 |
| 24 | $CH_3$ | H | 6-$CH_3$ | $CH_3$ | $CH_3$ | 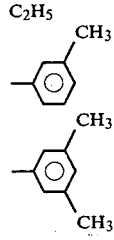 | O | 96–99 |

Table 1-continued

| Compound No. | $R^1$ | $R^2$ | $R^3$ | $R^4$ | $R^5$ | $R^6$ | Y | Melting point (°C.) or Refractive index |
|---|---|---|---|---|---|---|---|---|
| 25 | $CH_3$ | H | 6-$CH_3$ | $CH_3$ | $CH_3$ | $C_2H_5$–⟨O⟩–$C_2H_5$ | O | 72–74 |
| 26 | $CH_3$ | H | 6-$CH_3$ | $CH_3$ | $CH_3$ | i-$C_3H_7$ | O | 68–72 |
| 27 | $CH_3$ | H | 6-$CH_3$ | $CH_3$ | $CH_3$ | –$(CH_2)_2$–O–$(CH_2)_2$–$OCH_3$ | O | $n_D^{21}$: 1,5038 |
| 28 | $CH_3$ | H | 6-$CH_3$ | $CH_3$ | $CH_3$ | –$CH_2$–CO–$OC_4H_6$ | O | $n_D^{21}$: 1,4947 |
| 29 | $CH_3$ | H | 6-$CH_3$ | $CH_3$ | $CH_3$ | –$CH_2$–$CH_2CN$ | O | 85–87 |
| 30 | $CH_3$ | H | 6-$CH_3$ | $CH_3$ | $CH_3$ | –$(CH_2)_2$–S–$C_2H_3$ | O | $n_D^{22}$: 1,5203 |
| 31 | $CH_3$ | H | 6-$CH_3$ | $CH_3$ | $CH_3$ | –$(CH_2)_2$–O–⟨C_6H_5⟩ | O | $n_D^{21}$: 1,5341 |
| 32 | $CH_3$ | H | 6-$CH_3$ | $CH_3$ | $CH_3$ | –$(CH_2)_2$–N–$(CH_3)_2$ | O | 108–12 (xHCl) |
| 33 | $CH_3$ | H | 6-$CH_3$ | $CH_3$ | $CH_3$ | –$CH_2$–CH=$CH_2$ | O | 77–79 |
| 34 | $CH_3$ | H | 6-$CH_3$ | $CH_3$ | $CH_3$ | –$CH_2$–C≡CH | O | $n_D^{21}$: 1,5164 |
| 35 | $CH_3$ | H | 6-$CH_3$ | $CH_3$ | $CH_3$ | –$CH_2$–$CH_2Cl$ | O | 79–80 |
| 36 | $CH_3$ | H | 6-$CH_3$ | $CH_3$ | $CH_3$ | –⟨C_6H_{11}⟩ | O | $n_D^{22}$: 1,5123 |
| 37 | $CH_3$ | H | 6-$CH_3$ | $CH_3$ | $CH_3$ | –$CH_2$–⟨C_6H_5⟩ | O | $n_D^{22}$: 1,5373 |
| 38 | $CH_3$ | H | 6-$CH_3$ | $CH_3$ | $CH_3$ | –$C_4H_9$ | S | $n_D^{23}$: 1,5270 |
| 39 | $CH_3$ | H | 6-$CH_3$ | $CH_3$ | $CH_3$ | –$CH_2$–$CCl_3$ | O | 64–65 |
| 40 | $CH_3$ | H | 6-$CH_3$ | $CH_3$ | $CH_3$ | $C_3H_7$ | | 83–84 |
| 41 | $CH_3$ | H | 6-$CH_3$ | $CH_3$ | $CH_3$ | –CH($CH_3$)–C≡CH | O | oil |
| 42 | $CH_3$ | H | 6-$CH_3$ | $CH_3$ | $CH_3$ | –$CH_2$–△ | O | 53–54 |
| 43 | $CH_3$ | H | 6-$CH_3$ | $C_2H_5$ | $CH_3$ | $CH_3$ | O | 105–06 |

The fungicidal activity of the compounds of this invention is illustrated by the following examples wherein the compounds according to the present invention are each identified by the number (given in brackets) from preparative Examples 1 and 2.

EXAMPLE 3

Phytophthora test (tomato)/protective

Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated amount of emulsifier.

Yound tomato plants with 2 to 4 foliage leaves were sprayed with the spray liquid until dripping wet. The plants remained in a greenhouse for 24 hours at 20 deg. C. and at a relative atmospheric humidity of 70%. The tomato plants were then inoculated with an aqueous spore suspension of *Phytophthora infestans*. The plants were brought into a moist chamber with an atmospheric humidity of 100% and a temperature of 18°–20° deg. C.

After 5 days the infection of the tomato plants was determined. The assessment data were converted to percent infection: 0% meant no infection; 100% meant that the plants were totally infected.

In this test, for example, the following compounds exhibited a very good action which was significantly superior to that of the compounds known from the prior art: (1), (3), (4), (5), (6), (7), (11), (12), (15), (17), (18) and (34).

EXAMPLE 4

Phytophthora test (tomato)/systemic

Solvent: 4.7 parts by weight of acetone
Emulsifier: 0.3 part by weight of alkylaryl polyglycol ether
Water: 95 parts by weight The amount of active compound required for the desired concentration of the active compound in the watering liquid was mixed with the stated amount of solvent and the concentrate was diluted with the stated amount of water which contained the stated amount of the emulsifier.

Tomato plants grown in standard soil and having 2 to 4 foliage leaves were watered three times in the course of one week with 10 ml of the watering liquid, having the stated concentration of active compound, per 100 ml of soil.

The plants treated in this way were inoculated, after the treatment, with an aqueous spore suspension of *Phytophthora infestans*. The plants were brought into a humidity chamber at an atmospheric humidity of 100% and a temperature of 18 to 20 deg. C. After 5 days, the infection of the tomato plants was determined. The assessment data obtained were converted to percent infection. 0% denoted no infection and 100% denoted that the plants were totally infected.

In this test, for example, the following compounds exhibited a very good action which was superior to that of the compounds known from the prior art: (1) and (34).

It will be appreciated that the instant specification and examples are set forth by way of illustration and not limitation, and that various modifications and changes may be made without departing from the spirit and socpe of the present invention.

What we claim is:
1. An N-oxalyl-N-phenyl-aminoacid or ester thereof of the formula

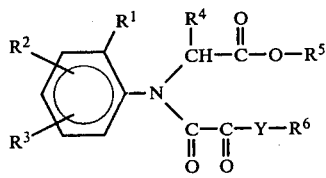

in which
R$^1$ represents hydrogen, straight-chain or branched alkyl with 1 to 4 carbon atoms, fluorine, chlorine or bromine,
R$^2$ represents hydrogen or straight-chain or branched alkyl with 1 to 4 carbon atoms,
R$^3$ represents hydrogen or straight-chain or branched alkyl with 1 to 4 carbon atoms,
R$^4$ represents hydrogen, straight-chain or branched alkyl with 1 to 4 carbon atoms or optionally substituted phenyl, the substituent(s) being selected from halogen, alkyl with 1 to 2 carbon atoms and halogenoalkyl with up to 2 carbon atoms and up to 3 identical or different halogen atoms,
R$^5$ represents hydrogen, straight-chain or branched alkyl or cyanoalkyl, each with 1 to 6 carbon atoms, alkenyl or alkynyl, each with 2 to 4 carbon atoms, halogenoalkyl with 1 to 4 carbon atoms and up to 5 halogen atoms, cycloalkyl with 3 to 7 carbon atoms, cycloalkylalkyl with 3 to 7 carbon atoms in the cycloalkyl part and 1 to 4 carbon atoms in the alkyl part, alkoxyalkyl, alkoxyalkoxyalkyl, alkoxycarbonylalkyl, alkylthioalkyl alkylsulphinylalkyl and alkylsulphonylalkyl, each with 1 to 4 carbon atoms in each alkyl part, aryl with 6 to 10 carbon atoms which is optionally substituted or aralkyl which is optionally substituted in the aryl part and has 6 to 10 carbon atoms in the aryl part and 1 to 4 carbon atoms in the alkyl part, the substituents on said aryl or aralkyl being selected from halogen, alkyl with 1 to 2 carbon atoms and halogenoalkyl with up to 2 carbon atoms and up to 3 identical or different halogen atoms, or dialkylaminoalkyl with 1 to 4 carbon atoms in each alkyl part,
R$^6$ represents straight-chain or branched alkyl or cyanoalkyl, each with 1 to 6 carbon atoms, alkenyl or alkynyl, each with 2 to 4 carbon atoms, halogenoalkyl with 1 to 4 carbon atoms and up to 5 halogen atoms, cycloalkyl with 3 to 7 carbon atoms, cycloalkyl-alkyl with 3 to 7 carbon atoms in the cycloalkyl part and 1 to 4 carbon atoms in the alkyl part, alkoxyalkyl, alkoxyalkoxyalkyl, alkoxycarbonylalkyl, alkylthioalkyl, alkylsulphinylalkyl and alkylsulphonylalkyl, each with 1 to 4 carbon atoms in each alkyl part, aryl with 6 to 10 carbon atoms which is optionally substituted or aralkyl which is optionally substituted in the aryl part and has 6 to 10 carbon atoms in the aryl part and 1 to 4 carbon atoms in the alkyl part, the substituents on said aryl or aralkyl being selected from halogen, alkyl with 1 to 2 carbon atoms and halogenoalkyl with up to 2 carbon atoms and up to 3 identical or different halogen atoms, or dialkylaminoalkyl with 1 to 4 carbon atoms in each alkyl part, aroxyalkyl which is optionally substituted in the aryl part and has 6 to 10 carbon atoms in the aryl part and 1 to 4 carbon atoms in the alkyl part, the substituents being selected from halogen, alkyl with 1 to 2 carbon atoms and halogenoalkyl with up to 2 carbon atoms and up to 3 identical or different halogen atoms, or epoxyalkyl with a total of 3 to 8 carbon atoms, or a group of the formula

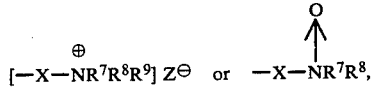

R$^7$, R$^8$ and R$^9$, which need not be identical, each represent alkyl with 1 to 4 carbon atoms,
X represents alkylene with 1 to 4 carbon atoms or alkylidene with 2 to 4 carbon atoms,
Y represents oxygen or sulphur and
Z represents the anion of an inorganic or organic acid.
2. A compound according to claim 1, in which
R$^1$ represents hydrogen, methyl, ethyl, n-propyl, isopropyl, n-butyl, isobutyl, sec.-butyl, tert.-butyl, fluorine, chlorine or bromine,
R$^2$ represents hydrogen, methyl, ethyl, n-propyl, isopropyl, n-butyl, isobutyl, sec.-butyl, or tert.-butyl,
R$^3$ represents hydrogen, methyl, ethyl, n-propyl, isopropyl, n-butyl, isobutyl, sec.-butyl, or tert.-butyl,
R$^4$ represents hydrogen, methyl, or phenyl which is optionally substituted by chlorine and/or by methyl and/or by ethyl,
R$^5$ represents hydrogen, methyl, ethyl, n-propyl, isopropyl, n-butyl, isobutyl, sec.-butyl, tert.-butyl, cyanoethyl, vinyl, allyl, propargyl, chloroethyl, cyclopropyl, cyclopropylmethyl, cyclohexyl, cyclohexylmethyl, methoxyethyl, ethoxyethyl, methylthioethyl, ethylthioethyl, methoxyethoxyethyl, butoxycarbonylmethyl, methylsulphinylethyl, ethylsulphinylethyl, methylsulphonylethyl, ethylsulphonylethyl, dimethylaminoethyl, diethylaminoethyl, phenyl, benzyl, or phenyl or benzyl substituted by chlorine and/or ethyl,
R$^6$ represents methyl, ethyl, n-propyl, isopropyl, n-butyl, isobutyl, sec.-butyl, tert.-butyl, cyanoethyl, vinyl, allyl, propargyl, chloroethyl, cyclopropyl, cyclopropylmethyl, cyclohexyl, cyclohexylmethyl, methoxyethyl, ethoxyethyl, methylthioethyl, ethylthioethyl, methoxyethoxyethyl, butoxycarbonylmethyl, methylsulphinylethyl, ethylsulphinylethyl, methylsulphonylethyl, ethylsulphonylethyl, phenyl, benzyl, phenyl or benzyl substituted by chlorine and/or methyl and/or ethyl, dimethylaminoethyl, diethylaminoethyl, phenoxyethyl, phenoxyethyl in which the phenyl part is substituted by methyl and/or ethyl, ethylene oxide-methyl, ethylene oxide-ethyl or a group of the formula

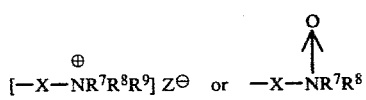

$R^7$, $R^8$, $R^9$ which need not be identical, each represent methyl or ethyl, X represents methylene, ethylene, ethylidene or propylidene, and Z represents a halide, nitrate, sulphate, phosphate, acetate, propionate, glycollate, lactate, malonate, tartrate, benzoate, methanesulphonate, p-toluenesulphonate, benzenesulphonate or methylsulphate anion.

3. A fungicidal composition containing as active ingredient a fungicidally effective amount of a compound according to claim 1 in admixture with a diluent.

4. A method of combating fungi which comprises applying to the fungi or to a habitat thereof, a fungicidally effective amount of a compound according to claim 1.

5. The method according to claim 4, in which the active compound is applied to soil, seed or a growing plant.

* * * * *